United States Patent [19]

Shibata

[11] Patent Number: 5,004,818

[45] Date of Patent: Apr. 2, 1991

[54] METHOD FOR PREPARATION OF NEPHRITOGENOSIDE

[76] Inventor: Seiichi Shibata, 40-11, Takadanobaba 4-chome, Shinjuku-ku, Tokyo, Japan

[21] Appl. No.: 381,493

[22] Filed: Jul. 18, 1989

[30] Foreign Application Priority Data

Jul. 21, 1988 [JP] Japan ................... 63-180378

[51] Int. Cl.$^5$ ............................... C07K 9/00
[52] U.S. Cl. ..................................... 530/322
[58] Field of Search .......................... 530/322

[56] References Cited

U.S. PATENT DOCUMENTS 4,382,887 10/1983 Shibata ................... 530/322

FOREIGN PATENT DOCUMENTS 58-18397  2/1983  Japan ................... 330/332
58-39697  8/1983  Japan ................... 530/322

OTHER PUBLICATIONS

S. Shibata, "Basement Membranes", *Proceedings of the International Symposium on Basement Membranes*, held in Mashimo (Japan) on Jun. 24–26, 1985, pp. 25–37, published by Elsevier Science Publishers, Amsterdam, 1985.
Connective Tissue Research, 1987, vol. 16, pp. 153–162.

*Primary Examiner*—Lester L. Lee

[57] ABSTRACT

In a method for preparing nephritogenoside from human placenta, rat kidney or other organs, tissues containing many microvessels are excised from the organ and treated with a nonionic surface active agent, especially, Triton X 100. Thus obtained precipitates are digested with trypsin and subjected to a chromatography treatment. Introduction of the nonionic surface active agent treatment enables simplification of the digestion step as well as a drastic improvement in yield.

10 Claims, 3 Drawing Sheets

METHOD FOR PREPARATION OF NEPHRITOGENOSIDE

BACKGROUND OF THE INVENTION

1. Field of the Invention

The present invention relates to a method for preparation of nephritogenoside, a substance having an ability to induce glomerulonephritis in animals. More specifically, the invention relates to a method for effectively and readily preparing nephritogenoside from some organs of various animals including human being and especially from human placenta at low cost.

2. Description of the Prior Art

Nephritogenoside is a glycopeptide having a structural formula shown in the attached FIG. 1. The glycopeptide has been isolated from rat kidney by the present applicant while he made investigations to purify an antigen of Masugi's glomerulonephritis. The glycopeptide has a specific ability that a single injection of the substance to a homologous or heterologous animal can induce glomerulonephritis in the animal without the aid of its immunological mechanism, and the induced glomerulonephritis will lead to contracted kidney without fail. This is the same progress as can be observed in human chronic glomerulonephritis. In addition, the substance can be extracted from tissues of normal animals (including healthy human being) and has a specificity that it induces glumerulonephritis in homologous animals.

The glycopeptide is expected, therefore, to perform a very important part in studying possible causes and therapeutic treatments of human glomerulonephritis. It also arrests much attention of medical and pharmaceutical fields to its wide applications and potential development of a therapeutic agent for human glomerulonephritis which may be obtained by making some modifications in the structure of nephritogenoside.

The previous investigations made by the applicant revealed that nephritogenoside exists not only in rats but in other animals such as human being, dogs, rabbits, cattles and pigs and that it is widely distributed throughout the body including lung, heart, aorta and placenta rather than only in kidney. This fact can be explained by its presence in basement membrane of microvessels which exist in those organs in a large quantity.

A previous method for preparation of nephritogenoside is well known to those skilled in the art.

According to that method, which was disclosed in U.S. Pat. No. 4,382,887 by the present applicant, nephritogenoside can be prepared by using kidney excised from rat.

More specifically, renal cortex is first excised from rat kidney to collect glomeruli and thus collected glomeruli are sonicated to collect glomerular basement membrane (GBM). The GBM is digested with trypsin for a short time (3 hours) and centrifuged to take the supernatant liquid, which is then dialyzed and lyophilized. Thus obtained powder is further digested with different proteinases (for example, trypsin, collagenase, and pronase) in succession to a possible minimum size and ultracentrifuged to take the supernatant liquid, which is then dialyzed and lyophilized. Next, the substance obtained is subjected to zone electrophoresis to collect only the first half of the glycopeptide peak exhibiting anthrone reaction. The collected substance is treated with trichloroacetic acid to take the supernatant liquid, which is dialyzed and separated through SEPHADEX G 200 or BIOGEL P 300 column chromatography. Of the two sugar peaks obtained, void volume fractions are collected for dialysis, and components which remain in the dialysis membrane are desalted and condensed to be subjected to DEAE cellulose column chromatography for purification.

Alternatively, a chemical synthesis method has been developed (Japanese Patent Publications No. 11598/84 and No. 26398/85) to prepare the same substance. According to it, glucose is bonded in sequence to produce the sugar moiety of the above glycopeptide and then the peptide moiety is bonded to the sugar moiety through N-glycoside bonding.

The first previous method in which rat kidney is used as the starting material adopts very complicated steps for preparation, and yields only 5 to 6 mg of nephritogenoside from kidneys of 1,200 rats. This low yield and resultant economic problems were one of the subjects the applicant must continue to study.

Also the second previous method to prepare the glycopeptide through chemical synthesis has a complicated step to bond glucose which comprises the sugar moiety. In addition, on forming N-glycoside bonding between the sugar chain moiety and peptide chain moiety, $\beta$-bonds besides desired $\alpha$-bonds are formed. When removing all products having the $\beta$-bonds, some $\alpha$-bond losses cannot be avoided, resulting in a low yield.

SUMMARY OF THE INVENTION

It is, therefore, an object of the present invention to provide a novel method for preparation of nephritogenoside which can be a solution to those problems of the previous methods.

According to the present method, some organs of various animals including human being can be used as the starting material, and excised tissues containing many microvessels are treated with a nonionic surface active agent. Through this treatment, a large amount of undesired components which comprise the tissues together with desired active components (nephritogenoside) can be made soluble and removed. The applicant has found that this serves to considerably simplify the steps beginning with the digestion and to provide an effective and simple isolation of nephritogenoside at low cost, and finally made the present invention.

In the method for preparation of nephritogenoside according to the present invention, tissues containing many microvessels are excised from various organs and treated with a nonionic surface active agent in an EDTA-containing physiological saline solution. Thus obtained precipitates are washed in a physiological saline solution and water in succession to remove the nonionic surface active agent, EDTA, and salt. The washed precipitates are digested with trypsin and centrifuged to take the supernatant liquid, which is then subjected to a chromatography treatment to separate nephritogenoside.

DESCRIPTION OF THE PREFERRED EMBODIMENT

Figure 1:
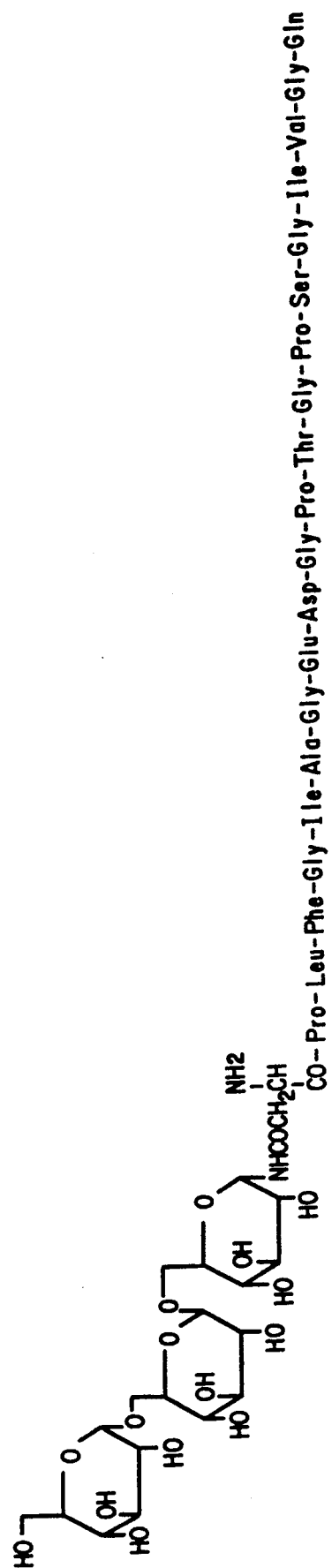
FIG. 1 shows structure of nephritogenoside.

Now the steps of the present method are described below in detail referring to the case that human placenta is the starting material. The human placenta, after amnion and the placenta marginal portion have been removed, consists of vascular trees called villi and spaces called intervillous spaces which surrounds the vascular trees. The villi consist of vessels ranging from microvessels to capillary vessels and are advantageous to collect tissues containing the microvessels in which nephritogenoside exists.

A. Collection of tissues containing many microvessels (villi) from placenta

Upon childbirth, human placenta delivered is put into 1 l of 0.9 % NaCl solution (pH 7.5) containing 20 mM EDTA and kept at a cold place.

The same EDTA-containing NaCl solution is introduced into the placenta through the unbilical cord vena to remove blood thoroughly from the placenta. From thus treated placenta which appears pink, amnion and the placenta marginal portion are removed, and then the placenta is cut into pieces with scissors and put into a mixer (excluding large vessels). The mixed placenta is passed through a plastic sieve of midium mesh (5 mm) to discard those left on the sieve (including large vessels). Those passing through the sieve are passed further through a plastic sieve of smaller mesh (0.5 to 1 mm) to collect almost all the vascular trees left on it. At this stage, those vascular trees appear white because blood protein is removed. The collected vascular trees are put into the mixer together with a physiological saline solution and agitated at high speed to destroy the trees and collect microvessels (villi) floating on the solution (about 95% of the destroyed trees are floating).

B. Treatment with a nonionic surface active agent

Thus collected villi are put into 10 mA EDTA solution containing a nonionic surface active agent and agitated thoroughly.

Through this treatment, a large amount of undesired components which comprise the villi together with desired components (nephritogenoside) can be made soluble and removed.

The nonionic surface active agents applicable to this treatment include polyethylene glycol alkyl ether and polyethylene glycol alkylphenyl ether types, for example, Triton X 100 and Triton NE manufactured by Rhome & Haas.

The dose of nonionic surface active agent is at least 0.002 cc, preferably 0.005 to 0.02 cc per 1 g (wet weight) of microvessels.

After 2 to 3 hour agitation, precipitates left insoluble are collected and sonicated in 10 mM EDTA solution to remove the surface active agent with an appropriate action taken to avoid the solution temperature from rising. This removal is repeated serveral times. The removal of the surface active agent may be considered complete if the supernatant liquid is clear and free of bubbles (due to the agent).

The precipitates are suspended in distilled water and centrifuged at low speed to remove the EDTA. During the removal of the surface active agent and EDTA as described above, it is preferrable to carry out at least one gravitational sedimentation operation rather than centrifugation to remove impurity.

Next, the supernatant liquid is decanted and the precipitates are lyophilized.

C. Digestion with trypsin

The samples obtained from the above steps are digested with trypsin (for 3 hours). The digestion conditions are as follows:

Buffer: 0.1 M Tris HCl (pH 8.1)—10 mM $CaCl_2$
Sample concentration: 25 mg/ml
Trypsin concentration: 1/30 (weight/weight) of the samples After 3 hour digestion, the samples are centrifuged in a refrigerated centrifuge at 7000 rpm (8900 G) for 30 min. to take the supernatant liquid. The separated precipitates are digested on the same conditions as described above (for 3 hours) and centrifuged to separate the supernatant liquid. This supernatant liquid is added to the previously obtained supernatant liquid, dialyzed and lyophilized.

D. Isolation of nephritogenoside

1. BIOGEL A 1.5 m column only

The lyophilized powder obtained from the trypsin digestion step is dissolved into a physiological saline solution containing a buffer and subjected to a BIOGEL A 1.5 m column (a trade name of Bio-Rad) for purification.

The column chromatography conditions are as follows:

Buffer; 0.3 M NaCl—50 mM Tris HCl (ph 7.6)
Elution rate: 9 to 10 sec./drop (200 drops/fraction)

After separation, each fraction containing a certain amount of eluent is examined on its 280 mn absorbance as well as the nephritogenoside content through the ELISA method [Clin. exp. Immunol. 51 595–599 (1983)] in which anti-nephritogenoside (anti-NG) rat serum is used.

Figure 2:
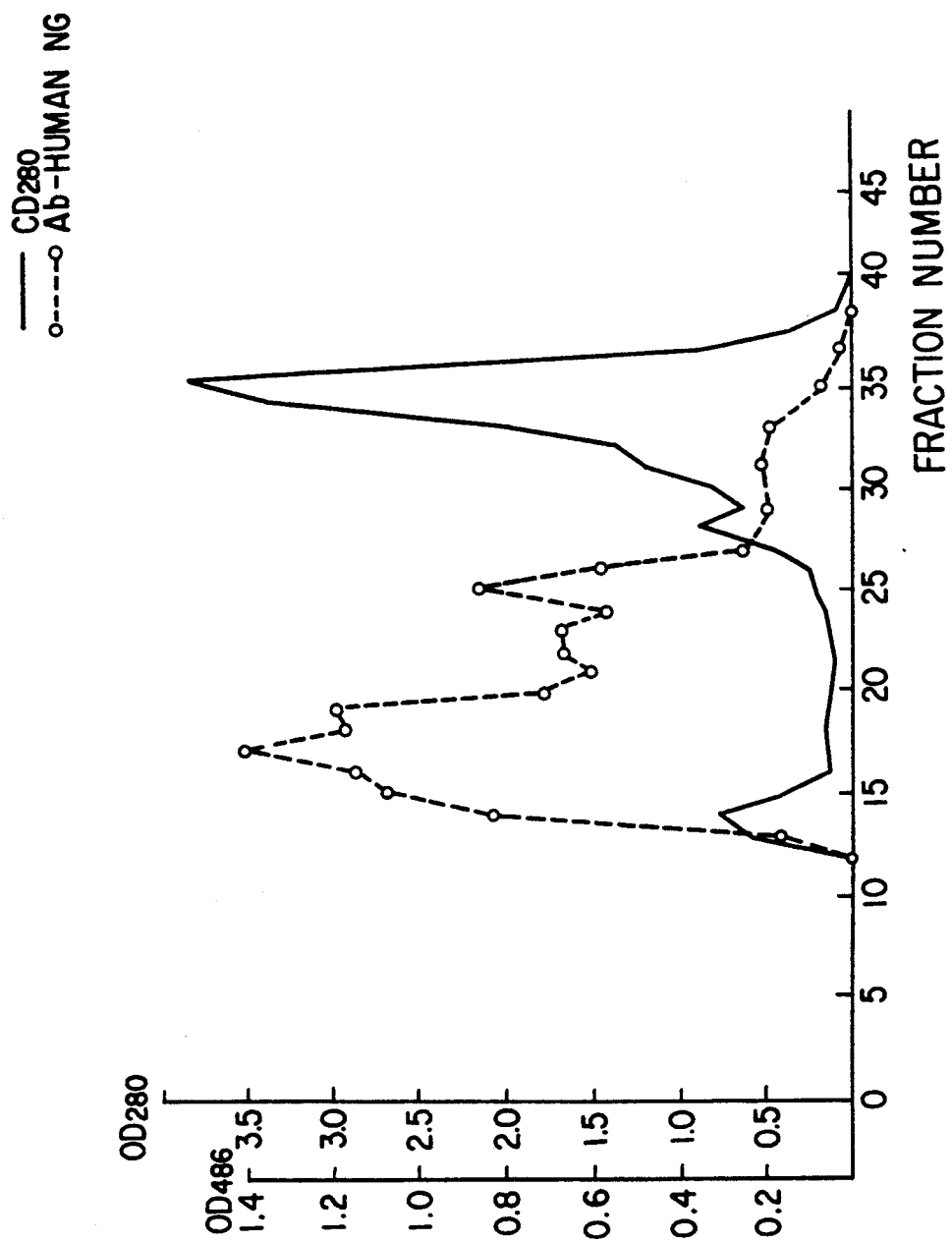
FIG. 2 is a column-chromatographic chart showing the results of the ELISA (Enzyme linked immunosorbent assay) method and 280 nm absorbance of each fraction which is separated in a BIOGEL A 1.5 m column from the trypsin-digested product of the Triton-treated human placenta.

As shown in FIG. 2, a small 280 nm absorption peak appears at void volume fractions and the subsequent absorption curve is kept flat before a large absorption peak around the fraction No. 30. On the other hand, the nephritogenoside activity peaks examined through the ELISA method are gathered between the two 280 nm absorption peaks. Therefore, the fractions (No. 14 to 27) between those peaks are combined to collect nephritogenoside. If necessary, collected nephritogenoside is further purified with HPLC.

2. DEAE-cellulose column and BIOGEL A 1.5 m column

The purification can be carried out by another method.

The lyophilized powder obtained from the above step C is dissolved into a physiological saline solution containing a buffer and then poured into a DEAE-cellulose column for purification.

The column chromatography conditions are as follows:

Buffer: 20 mM Tris HCl (pH 7.6)
Elution rate: 9–10 sec./drop (200 drops/fraction)

After separation, each fraction containing a certain amount of eluent is examined on its 280 nm absorbance as well as the distribution of NG activity through the ELISA method in which anti-NG rat serum is used.

Figure 3A:
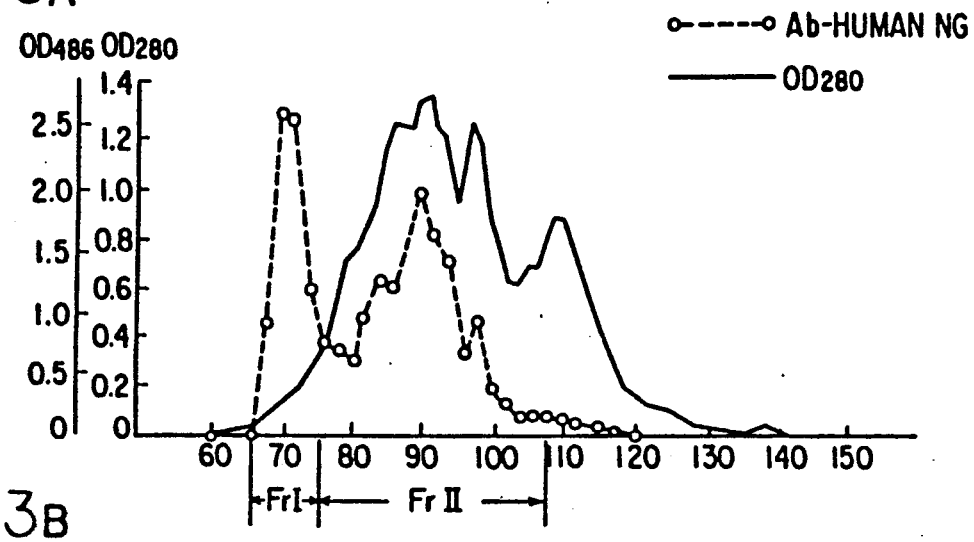
FIG. 3 is a chart similar to FIG. 2 showing the results of each fraction which is separated in a DEAE-cellulose column from the same trypsin-digested product (3A) and the results of each fraction which is separated in purification with BIOGEL A 1.5 m column of the fractions I and II of FIG. 3A (3B and 3C).

As shown in FIG. 3A, the NG activity measured through the ELISA method is divided into two peaks. There is no peak of 280 nm absorbance at the first peak (fraction I), while there is a large peak of 280 nm absorbance at the second peak (fraction II).

Figure 3B:
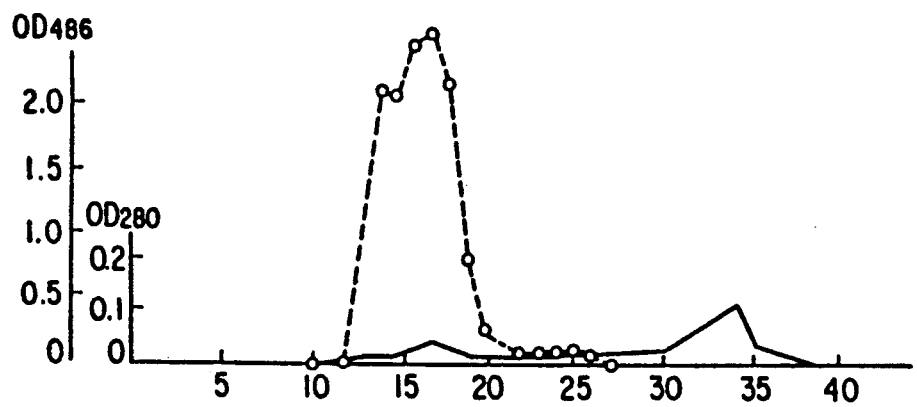

The fraction I is further poured into a BIOGEL A 1.5 m column on the same conditions as described above 1 to check the purity. As shown in FIG. 3B, the nephritogenoside activity exists only at earlier fractions and the content of components exhibiting 280 nm absorbance is remarkably low, which shows it is purified to a considerable extent.

Figure 3C:
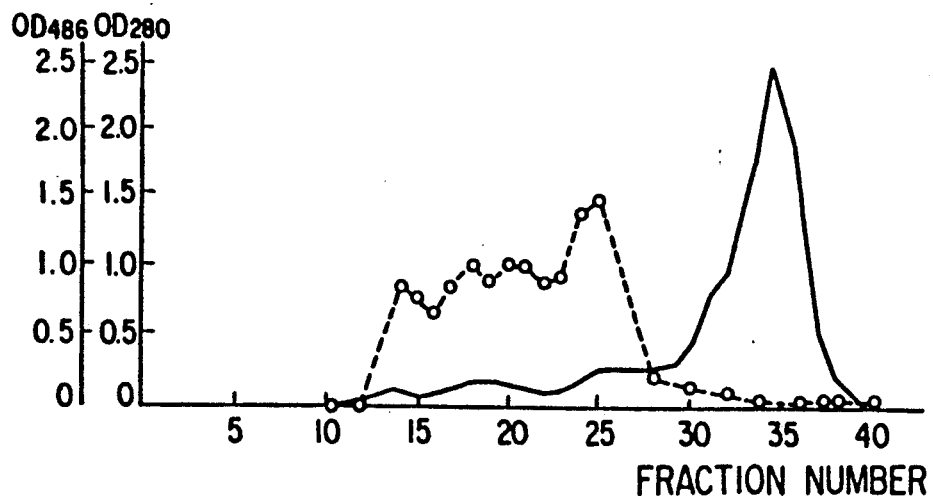

The fraction II is poured into a BIOGEL A 1.5 m column similarly to the fraction I for further separation. As shown in FIG. 3C, the nephritogenoside activity shows a column chromatographic pattern similar to that of the above 1.

From the foregoing, the isolation process using the DEAE-cellulose column and the BIOGEL A 1.5 m column in succession can produce purer nephritogenoside than the direct isolation through the BIOGEL A 1.5 m column.

According to the present invention, tissues containing many microvessels are excised from some organs of various animals including human being. The excised tissues are not directly digested with trypsin but, before trypsin-digestion, treated with a nonionic surface active agent to remove undesired components of the tissues as much as possible in a form of supernatant liquid. As compared with the previous methods using rat kidney as the starting material, therefore, the present method does not require collagenage, pronase, and other proteinase digestion steps to thoroughly digest the undesired components. The yield can be improved drastically and desired nephritogenoside can be prepared at low cost.

The invention will be understood more readily by reference to the following examples; however, these examples are intended to illustrate the invention and are not to be construed to limit the scope of the invention.

EXAMPLE 1

Three human placentas (1.7 kg; wet weight) were dipped into 0.9 % NaCl solution (pH 7.5) containing 20 mM EDTA and kept at a cold place. Those placentas were treated as described in the above step A to collect 0.15 kg (wet weight) of villus samples.

The villus samples were suspended in 2 l of 10 mM EDTA solution containing 0.1% Triton X 100 and agitated with a magnetic stirrer for 3 hours. Then the samples were stood still and slightly centrifuged to remove the supernatant liquid. Thus obtained precipitates were sonicated in 10 mM EDTA solution in a sonicator for 10 min. with several blocks of ice added to the solution to prevent any solution temperature rising. This operation was repeated three times to remove the Triton.

As a final stage, the precipitates were put into a 4 l beaker and suspended in distilled water. The suspension was centrifuged at low speed and the supernatant liquid was decanted to remove the EDTA. Thus obtained precipitates were lyophilized. The lyophilized product was about 10 g.

Thus obtained samples (10 g) were dissolved into 0.1 M Tris HCl (pH 8.1)—10 mM $CaCl_2$ solution in the amount of 25 mg/ml and 0.33 g of trypsin was added to the solution. The mixture was shaked at 37° C. for 3 hours. After completion of the digestion, the mixture was centrifuged in a refrigirated centrifuge at 7000 rpm (8900 G) for 30 min. to collect the supernatant liquid. The separated precipitates were trypsindigested again similarly to the first digestion and centrifuged to collect another supernatant liquid. The second liquid was added to the first liquid, and the resultant liquid was dialyzed and lyophilized to collect digested products. [Yield: 2.49 g].

The digested products were separated with a BIOGEL A 1.5 m column for purification as described in the above step D.1. The fractions No. 14 to 27 were combined to obtain nephritogenoside. [Yield: 583 mg].

COMPARISON 1

10 g of villus samples excised from human placentas were treated similarly to the Example 1, except that the washing with Triton X 100 was omitted.

Nephritogenoside was obtained only in trace amounts. This is because most of villus components to be made soluble and removed through a Triton treatment were left unchanged and those components could not be digested completely through a short-period digestion with trypsin only. Therefore, undesired components must be digested thoroughly with other proteinases (for example, pronase and collagenase).

EXAMPLE 2

Nephritogenoside was prepared from rat kidney.

40 rat kidneys were pretreated to remove blood and then excised to collect renal cortex only. The renal cortex are tissues containing microvessels, glomeruli. 50 g of the obtained renal cortex was dispersed in 360 cc of 10 mM EDTA solution containing 0.1% Triton X 100 and agitated with a magnetic stirrer for 2 hours. After it was stood still, the supernatant liquid was decanted. The precipitates obtained were sonicated in 10 mM EDTA solution with a sonicator for 10 min. with several blocks of ice added to the solution prevent any solution temperature rising. This operation was repeated three times to remove Triton X 100.

Thus obtained precipitates were suspended in distilled water and centrifuged at low speed to separate the supernatant liquid for removal of EDTA. The precipitates were lyophilized. The lyophilized product was 690 mg.

The 690 mg sample was digested for purification similarly to the Example 1.

Nephritogenoside was obtained through purification with a BIOGEL A 1.5 m column. [Yield: 8 mg].

Although the previous methods produced only 5 to 6 mg of nephritogenoside from 1200 rat kidneys, the above method according to the present invention could produce almost the same amount of nephritogenoside from only 40 rats. This shows that the yield can be improved drastically.

COMPARISON 2

50 g of the renal cortex excised from rat kidneys similarly to the Example 2 was directly subjected to trypsin digestion without treatment with Triton X 100, and then purified. In this Comparison, nephritogenoside could be obtained only in trace amounts as in the Comparison 1.

While a preferred embodiment has been described, variations thereto will occur to those skilled in the art within the scope of the present inventive concepts which are delineated by the following claims.

What is claimed is:

1. A method for preparation of nephritogenoside, which comprises:
   (a) treating nephritogenoside-containing animal organ tissue containing many microvessels with a nonionic surface active agent in an EDTA containing physiological salt solution;
   (b) washing the precipitates thus obtained in a physiological salt solution and water in succession to remove said nonionic surface active agent, EDTA, and salt components;
   (c) digesting the washed precipitates with trypsin;
   (d) centrifuging the digested liquid to recover the supernatant liquid; and
   (e) subjecting the supernatant liquid to a chromatography treatment to separate nephritogenoside.

2. A method in the claim 1, wherein said nonionic surface active agent is a polyethylene glycol alkyl ether or polyethylene glycol alkylphenyl ether.

3. A method claimed in the claim 2, wherein said nonionic surface active agent is polyethylene glycol p-isooctylphenyl ether or polyethylene glycol nonylphenyl ether.

4. A method claimed in the claim 1, wherein said tissues containing many microvessels are those excised from organ selected from lung, heart, aorta, placenta and kidney.

5. A method claimed in the claim 1, wherein human placenta is used as the starting material.

6. A method claimed in the claim 1, wherein rat kidney is used as the starting material.

7. A method claimed in claim 1, wherein the chromatography treatment is carried out with a cross-inked agarose gel matrix iron-exchanger 1.5 m column.

8. A method claimed in claim 1, wherein the chromatography treatment is carried out with a DEAE cellulose column and a cross-linked agarose gel matrix iron exchanger 1.5 m column.

9. A method as claimed in claim 1, wherein said animal organ tissue containing many microvessels is excised from an animal organ.

10. A method as claimed in claim 1, wherein said tissue containing many microvessels is mammalian tissue.

* * * * *